United States Patent [19]

Kodras

[11] 4,215,994
[45] Aug. 5, 1980

[54] PROCESS FOR LIQUID-LIQUID SORBENT EXTRACTION

[76] Inventor: Rudolph Kodras, 412 S. Robinson St., Baltimore, Md. 21224

[21] Appl. No.: 508,642

[22] Filed: Sep. 23, 1974

[51] Int. Cl.$^2$ .............................................. G01M 31/00
[52] U.S. Cl. .................................. 23/230 B; 210/21; 210/29
[58] Field of Search ....................... 210/21, 24, 25, 29; 23/230 B, 267 R

[56] References Cited

U.S. PATENT DOCUMENTS

| | | | |
|---|---|---|---|
| 3,452,110 | 6/1969 | Cooley | 210/21 X |
| 3,485,592 | 12/1969 | Hathaway | 210/21 X |
| 3,625,652 | 12/1971 | Fujimoto et al. | 23/230 B |

OTHER PUBLICATIONS

Detection of Narcotic Drugs . . . Urine, Dole et al., JAMA, vol. 194, No. 4, Oct. 24, 1966.
Athin–Layer . . . Drug Abuse, Davidow et al., American Journal of Clinical Pathology, vol. 50, No. 6, 1968.

*Primary Examiner*—Charles N. Hart
*Assistant Examiner*—Ferris H. Lander

[57] ABSTRACT

This invention relates to a process for extraction in which a sorbent wetted with one of two immiscible fluids exchanges the first fluid (nonpolar) for the second fluid (polar) and whereupon the first fluid extracts the desired substance(s) from the second fluid.

4 Claims, No Drawings

PROCESS FOR LIQUID-LIQUID SORBENT EXTRACTION

This invention relates to a process for extraction in which a sorbent wetted with one of two immiscible fluids exchanges the first fluid for the second fluid whereupon the first fluid extracts the desired substance from the second fluid. The sorbent has a greater affinity for the second fluid.

It is an object of this invention to provide an improved process for contacting two immiscible or partially miscible fluids using the large surface area of a sorbent for intimate contact between the two phases for extraction of material.

It is a further object of this invention to provide an improved process for contacting fluids in a manner to insure instant attainment of equilibrium between the fluids and also the rapid separation of the resulting phases.

Another object of this invention is to provide an improved process for reversing the free phase and the bound phase on the sorbent for rapid extraction and separation of the resulting phases.

Other objects of this invention will be apparent from a reading of the specification.

Selection of the proper sorbent is important. The sorbent should be of small particle size and have a large surface area. It should not only have adsorptive properties for both phases but also have a greater affinity for the phase that will end up bound to the sorbent. Starting with diatomaceous earth wetted with chloroform, one adds water; the phases exchange resulting in free chloroform and water adsorbed on the diatomaceous earth.

The pharmaceutical industry, which synthesizes or recovers from naturally occurring substances thousand of complex organic chemicals for use as drugs, uses liquid extraction in an extremely large portion of its separation operations, since many of the products are heat-sensitive and cannot be subject to distillation. Many of these operations are done on a relatively small scale, so that batch extraction are not uncommon. Examples of some solvents used for specific drugs are:

butyl acetate for pencillin, petroleum ether for vitamin A, and progesterone,
acetone for estrone
ether for hydrostine,
chloroform for codeine, digitoxin, atropine and other alkaloids.

For toxicological analysis, hundreds of drugs from biological fluids are extracted with chloroform.

The invention is illustrated in the following example for toxicology. The specimen can be urine, gastric contents or blood containing one or more drugs such as morphine, codeine, amphetamine, meperidine, cocaine, propoxyphene, methadone, Valium, Librium, secobarbital, phenobarbital, Dilantin or Doriden. Into a 50 milliliter beaker 1.7 grams of diatomaceous earth and 7 milliliters of chloroform are added. The specimen such as blood is added directly into the beaker and stirred for about 30 seconds at which time the chloroform is released. The chloroform is clear and free of any suspended material. The chloroform is then decanted into a $16 \times 100$ mm tube. Tube is placed in a 60 degree centigrade heating block and a stream of air is directed into the tube until the solvent in the tube is evaporated to dryness. The dried tube is extracted with 50 lambda of methanol and spotted on a thin layer plate. Concentration of standard drugs are also spotted on the plate. The thin layer plate is allowed to develop with the proper solvent system. The plate is sprayed with a series of reagents that will produce colored spots with specific drugs. The spots which are the unknown drugs are identified by their color and Rf values. When standard drugs were extracted and treated in the above manner, recoveries 75% or higher were obtained.

Suitable sorbents can be silica gel, calcium sulfate, calcium chloride, sodium sulfate, calcium oxide, calcium chloride, sodium sulfate, activated clay, activated carbon, silica and charcoal.

Suitable polar fluids containing the desired substance for extraction can be any biological tissue or fluid such as blood, plasma, gastric contents, urine, intestinal contents, and plant extracts and other aqueous mixtures.

Suitable nonpolar fluids for extraction can be amyl acetate, butyl acetate, acetone, petroleum ether, diethyl ether, chloroform, benzene, carbon tetrachloride, and other organic solvents.

While in the foregoing specifications only a single embodiment has been set forth, it is to be understood that the invention is not to be limited to the specific embodiments thereof except as defined in the appended claims.

I claim:

1. A process for the extraction of a desired substance(s) in which a sorbent wetted with one of two immiscible liquids exchanges the first liquid (nonpolar) for the second liquid (polar) and whereupon the first liquid extracts the desired substance(s) from the second liquid.

2. A process according to claim 1 wherein the process comprises, in combination, the steps of: (a) mixing the sorbent with the first liquid (nonpolar phase): (b) adding the second liquid (polar phase and containing the desired substance(s); (c) mixing the sorbent and the second liquid until the liquids exchange positions; and (d) draining or decanting off the first liquid containing the desired substance(s).

3. A process according to claim 1 wherein the sorbent is diatomaceous earth, the polar liquid is a biological liquid such as urine, blood or gastric contents containing a drug and the nonpolar liquid is chloroform.

4. A process according to claim 1 wherein the sorbent is selected from the group consisting of silica gel, calcium sulfate, sodium sulfate, activated clay, activated carbon, silica and charcoal.

* * * * *